United States Patent [19]

Connor

[11] Patent Number: 5,671,747
[45] Date of Patent: Sep. 30, 1997

[54] ULTRASOUND PROBE HAVING INTERCHANGEABLE ACCESSORIES

[75] Inventor: Brian G. Connor, Stratham, N.H.

[73] Assignee: Hewlett-Packard Company, Palo Alto, Calif.

[21] Appl. No.: 590,976

[22] Filed: Jan. 24, 1996

[51] Int. Cl.⁶ .................................................. A61B 8/12
[52] U.S. Cl. ...................................... 128/662.06
[58] Field of Search ............... 128/660.01, 660.07, 128/660.05, 661.07, 662.03, 662.05, 662.06

[56] References Cited

U.S. PATENT DOCUMENTS

| | | | |
|---|---|---|---|
| 4,535,781 | 8/1985 | Hetz | 128/660 |
| 4,593,699 | 6/1986 | Poncy et al. | 128/662.03 |
| 4,742,829 | 5/1988 | Law et al. | 128/754 X |
| 4,794,931 | 1/1989 | Yock | 128/662.06 X |
| 4,877,033 | 10/1989 | Seitz, Jr. | 128/660.05 |
| 4,883,059 | 11/1989 | Stedman et al. | 128/660.01 |
| 5,076,279 | 12/1991 | Arenson et al. | 128/662.05 |
| 5,152,293 | 10/1992 | Vonesh et al. | 128/662.03 |
| 5,284,147 | 2/1994 | Hanaoka et al. | 128/662.06 |
| 5,381,795 | 1/1995 | Nordgren et al. | 128/663.01 |

*Primary Examiner*—Francis Jaworski
*Attorney, Agent, or Firm*—John L. Imperato

[57] ABSTRACT

In the present invention, an intraoperative ultrasound transducer probe, or intraoperative probe, has a housing, to which, interchangeable accessories may be attached. The interchangeable accessories adapt the intraoperative probe's shape to provide access to a patient's body parts in confined spaces in intraoperative environments. In one embodiment of the present invention a first interchangeable accessory has an extension handle that may be attached to the intraoperative probe to enable an operator to reach into surgical incisions and view the patient's body parts. In an alternate embodiment of the present invention a second interchangeable accessory has a finger cuff for attaching the intraoperative probe to an operator's finger. The finger cuff may be used in place of the extension handle, providing access to a patient's body parts in confined spaces, such as the posterior side of the heart for epicardial imaging during open heart surgery. Since the interchangeable accessories are separable from the intraoperative probe, they are easily sterilized and may be disposed of after use. The interchangeable accessories used to adapt the intraoperative probe's shape have low manufacturing cost relative to the cost of multiple dedicated probes, reducing the overall cost of an ultrasound imaging system.

11 Claims, 2 Drawing Sheets

ULTRASOUND PROBE HAVING INTERCHANGEABLE ACCESSORIES

FIELD OF THE INVENTION

This invention discloses an ultrasound probe having interchangeable accessories for maneuvering the ultrasound probe in diverse intraoperative ultrasound medical imaging applications.

BACKGROUND OF THE INVENTION

At present, medical ultrasound transducer probes, or probes, are used in dedicated ultrasound imaging environments. As probes are increasingly used in intraoperative, or surgical, applications the imaging environments become substantially less predictable. A probe's shape may limit its utility in the confined spaces often encountered during surgery. In fact, the probe's shape may preclude an operator from viewing a patient's body parts during critical surgical procedures.

A probe disclosed by Nordgren et al. in U.S. Pat. No. 5,381,795 has a shape resembling a tiny leg and foot. When this probe is inserted into a surgical incision, a surgeon may ultrasonically examine organs and tissues peripheral to the surgical site. However, the shape of this probe may limit its maneuverability and utility, especially for viewing the posterior side of the heart during open heart surgery. Hanaoka et al. disclose a finger probe in U.S. Pat. No. 5,284,147 that is attachable to an operator's finger and may be maneuverable in such intraoperative environments. Although the finger probe enables viewing of certain body parts during surgery, the attachment of the finger probe to an operator's finger may limit the insertion depth of the probe into a surgical incision or the size of the finger and the finger probe may preclude insertion into small incisions during vascular surgery. Although several probes, each having a dedicated shape, may be employed by an operator to view various tissues and organs during surgery, the dedicated probes are expensive and burden the cost of an ultrasound imaging system. In addition, each probe must be sterile when introduced into the sterile surgical environment.

SUMMARY OF THE INVENTION

In the present invention, an intraoperative ultrasound transducer probe, or intraoperative probe, has a housing, to which, interchangeable accessories may be attached. The interchangeable accessories adapt the intraoperative probe's shape to provide access to a patient's body parts in confined spaces in intraoperative environments. In one embodiment of the present invention a first interchangeable accessory has an extension handle that may be attached to the intraoperative probe to enable an operator to reach into surgical incisions and view the patient's body parts, even those body parts under unincised tissue. In an alternate embodiment of the present invention a second interchangeable accessory has a finger cuff for attaching the intraoperative probe to an operator's finger. The finger cuff may be used in place of the extension handle, providing access to a patient's body parts in confined spaces, such as the posterior side of the heart for epicardial imaging during open heart surgery.

Since the interchangeable accessories are separable from the intraoperative probe, they are easily sterilized and may be disposed of after use. The interchangeable accessories used to adapt the intraoperative probe's shape have low manufacturing cost relative to the cost of multiple dedicated probes, reducing the overall cost of an ultrasound imaging system.

DETAILED DESCRIPTION OF THE PREFERRED EMBODIMENT

Figure 1A:
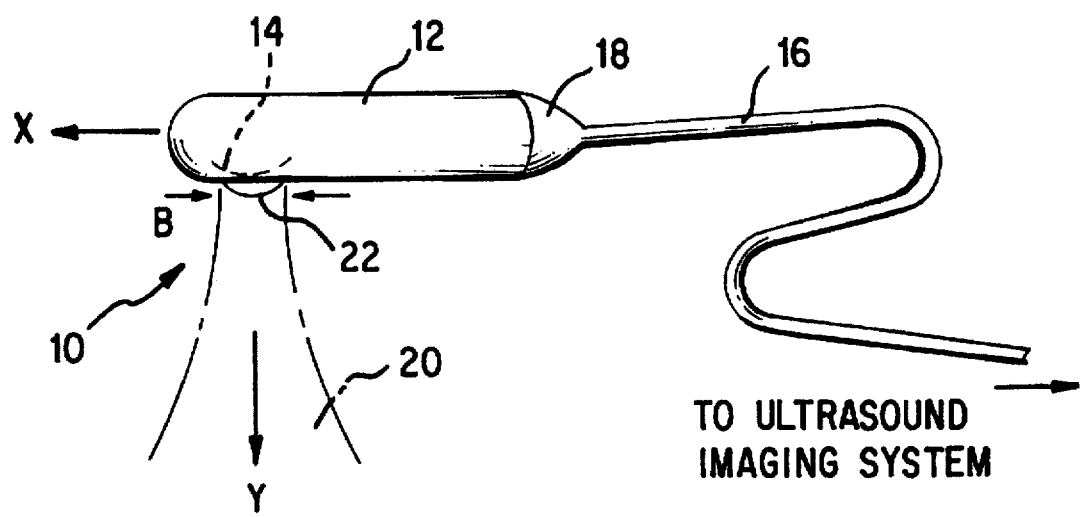
FIGS. 1A and 1B show intraoperative probes of the present invention.
Figure 1B:
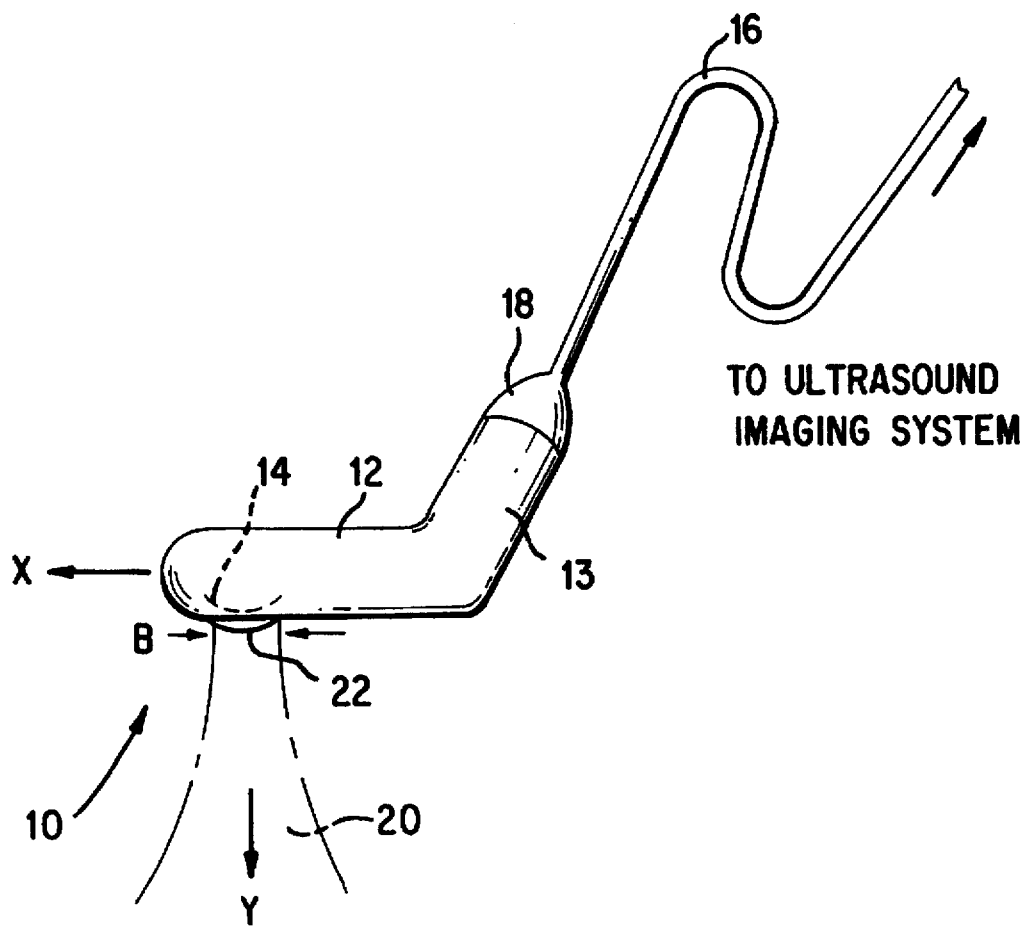

FIG. 1A and FIG. 1B show intraoperative probes 10 of the present invention. A housing 12 encases an array 14 of ultrasound transducer elements, electronic interconnections (not shown) to the array 14 and mechanical components (not shown) for mounting the array 14 within the housing 12. The electronic interconnections to the array 14 and the mechanical components used to mount the array 14 within the housing 12 are known in the art and are present in various ultrasound probes, such as the HP21275A and the HP21366A, commercially available from the Hewlett-Packard Company.

A flexible cable 16 provides connection of the array 14 to an ultrasound imaging system (not shown). The ultrasound imaging system transmits electronic signals which propagate through the flexible cable 16 to the array 14. The ultrasound imaging system also receives electronic signals through the cable 16 from the array 14. An ultrasound image of a patient's body parts is produced on a display of the ultrasound imaging system based on analysis of the transmitted and received electronic signals.

A strain relief 18 mechanically reinforces the interface between the housing 12 and the flexible cable 16 and provides a seal at the interface between the housing 12 and the flexible cable 16. The array 14 produces a planar ultrasound beam 20 having a beam axis Y, perpendicular to the longitudinal axis X of the housing 12. The ultrasound beam 20 is emitted through an acoustic window 22 formed in the housing 12.

In FIG. 1A, the housing 12 is cylindrical in shape and in this example is one half inch in diameter and one and one half inches in length. Alternatively, as shown in FIG. 1B, the housing 12 also has a bent portion 13 that is angled relative to the longitudinal axis X. The bent portion 13 of the housing 12 may provide the intraoperative probe 10 increased maneuverability around body structures in intraoperative environments. Either housing 12 shape provides for easy attachment of interchangeable accessories (shown in FIGS. 2 and 3) and the housing 12 may be rotated to orient the ultrasound beam 20 relative to a patient's body parts (not shown).

The array 14 shown forms a convex arc to provide the ultrasound beam 20 a width B proximal to the window 22. This enables an operator to have a field of view of width B for viewing a patient's body parts proximal to the window 22 of the housing 12. The width B depends on the radius of the convex arc of the array 14 and also on the number of ultrasound transducer elements within the array 14.

Alternatively, a linear, non-curved array 14 may also be used and the array orientation within the housing 12 may be chosen to correspondingly redirect the beam axis Y and planar ultrasound beam 20, relative to the longitudinal axis X.

Figure 2:
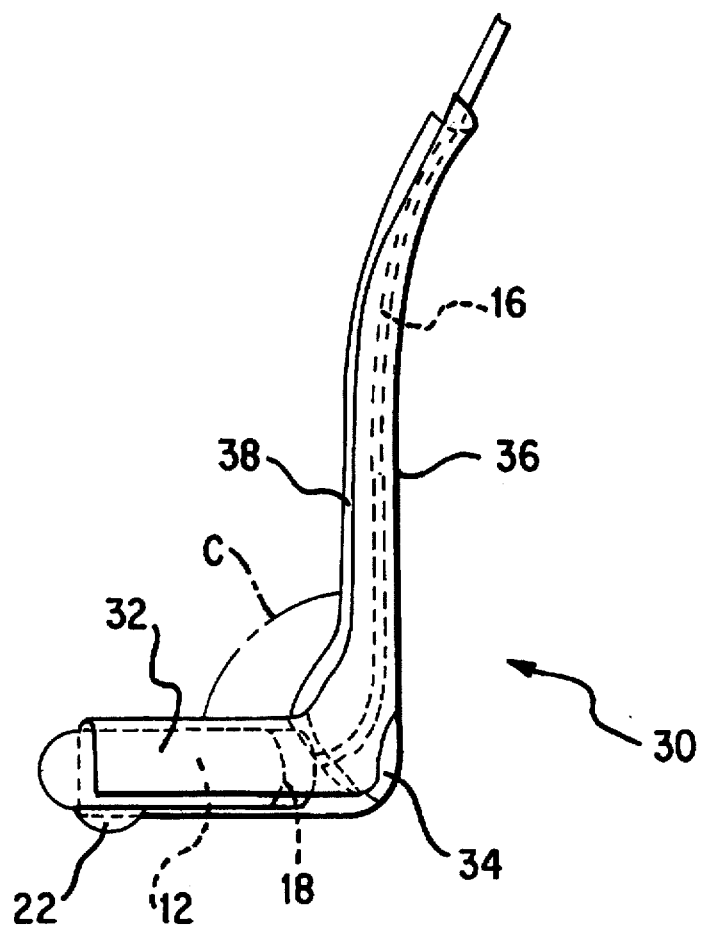
FIG. 2 shows an interchangeable extension handle constructed in accordance to a first preferred embodiment of the present invention.

FIG. 2 shows an interchangeable extension handle 30 for use with the intraoperative probe 10 in the first embodiment of the present invention. A clip 32 provides attachment of the extension handle 30 to the housing 12. The housing 12 is threaded through an aperture 34 at the junction formed by a shaft threaded through an aperture 34 at the junction formed by a shaft 36 and the clip 32. During use, the housing 12 is then seated in the clip 32. In this example, the clip 32 comprises a deformable semi-circular ring that deforms enough to receive and then firmly hold the housing 12 of the intraoperative probe 10. Although the housing 12 is firmly held within the clip 32, the rotational orientation of the housing 12 may be adjusted within the clip 32 by an operator. The shaft 36 of the extension handle 30 contains a trough 38 to accommodate the flexible cable 16.

Once the housing 12 is seated in clip 32 and the cable 16 is seated in the trough 38, an operator may hold the shaft 36 and place the window 22 of the housing 12 in proximity of the patient's body parts to be viewed. The angle C formed between the shaft 36 and the clip 32 is shown, but not restricted, to between 90° and 180°. The angle C may be formed to suit a particular surgical environment. For example, an angle C equal to 180° may provide access into incisions in a patient's abdomen or chest cavity.

Figure 3:
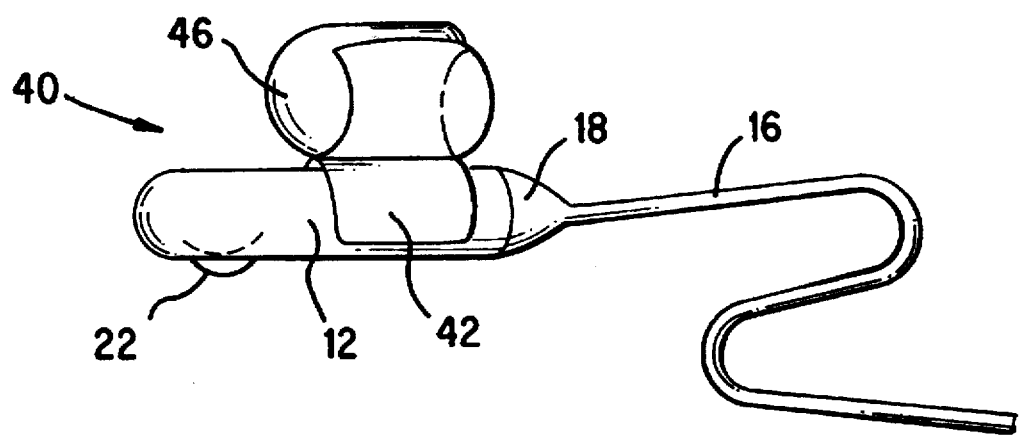
FIG. 3 shows an interchangeable finger cuff constructed in accordance to a second preferred embodiment of the present invention.

FIG. 3 shows an interchangeable finger cuff 40 for use with the intraoperative probe 10 in a second embodiment of the present invention. A clip portion 42 provides attachment of the finger cuff 40 to the housing 12. During use, the housing 12 is firmly seated in clip portion 42. In this example, the clip portion 42 comprises a deformable semi-circular ring that deforms enough to receive and then firmly hold the housing 12 of the intraoperative probe 10. Although the housing 12 is firmly held operator. The operator's finger (not shown) may then be inserted into the cuff portion 46 and using the finger, the operator may position the window 22 of the housing 12 in proximity of the patient's body parts to be viewed.

The extension handle 30 of FIG. 2 and the finger cuff 40 of FIG. 3 may be formed from plastic, metal or other suitable material and may be sterilized before each use, or since each of the interchangeable accessories 30, 40 have low manufacturing cost, they may be disposed of after each use.

Once the intraoperative probe 10 is brought into the sterile surgical environment, only the interchangeable accessories 30, 40 that are subsequently introduced into the surgical environment must be sterile. Since the interchangeable accessories are separable from the probe, they are easily sterilized. The interchangeable accessories 30, 40 adapt the intraoperative probe's shape for use in the surgical environment. Relative to the cost of multiple dedicated probes, the intraoperative probe 10 with the interchangeable accessories 30, 40 may significantly reduce the overall cost of an ultrasound imaging system.

I claim:

1. An intraoperative ultrasound transducer probe, comprising:

a housing having a window at one end;

an array of ultrasound transducer elements within the housing and aligned with the window;

a flexible cable for connecting the one end to an ultrasound imaging system; and an accessory having a handle and a deformable semi-circular ring removably fastening to the housing.

2. The intraoperative ultrasound transducer probe of claim 1, the handle comprising a shaft protruding from the clip.

3. The intraoperative ultrasound transducer probe of claim 2, the shaft of the handle having an open trough captively holding the flexible cable.

4. The intraoperative ultrasound transducer probe of claim 1, the array of ultrasound transducer elements forming a convex arc and producing a planar ultrasound beam perpendicular to a longitudinal axis of the housing.

5. The intraoperative ultrasound transducer probe of claim 1, the array of ultrasound transducer elements forming a linear arrangement.

6. The intraoperative ultrasound transducer probe of claim 1, wherein the handle comprises a finger cuff.

7. An intraoperative ultrasound transducer probe for use with an ultrasound imaging system, comprising:

a cylindrical housing having a longitudinal axis and having a first end and a second end;

an array of ultrasound transducer elements within the housing at the first end;

an acoustic window attached to the housing and aligned with the array;

a flexible cable attached to the second end, the flexible cable connecting the array to the ultrasound imaging system; and a finger cuff removably fastening to the cylindrical housing.

8. The intraoperative ultrasound transducer probe of claim 7, the finger cuff further including a deformable semi-circular ring attachable to the cylindrical housing and a cuff portion for accommodating an operator's finger.

9. The intraoperative ultrasound transducer probe of claim 8, the array of ultrasound transducer elements forming a convex arc.

10. An intraoperative ultrasound transducer probe for use with an ultrasound imaging system, comprising:

a cylindrical housing having a longitudinal axis and having a first end and a second end;

an array of ultrasound transducer elements within the housing at the first end;

an acoustic window attached to the housing and aligned with the array;

a flexible cable attached to the second end, the flexible cable connecting the array to the ultrasound imaging system;

a deformable semi-circular ring removably fastening to the cylindrical housing; and a shaft connected to the deformable semi-circular ring and protruding from the deformable semi-circular ring for being held by an operator, the shaft having an open trough for captively holding the flexible cable.

11. The intraoperative ultrasound transducer probe of claim 10, the array of ultrasound transducer elements forming a convex arc.

\* \* \* \* \*